United States Patent [19]

Dryden, Jr. et al.

[11] 4,086,234
[45] Apr. 25, 1978

[54] PROCESS FOR THE PREPARATION OF TERTIARY AMINES

[75] Inventors: Hugh Latimer Dryden, Jr.; Robert A. Erickson, both of Deerfield, Ill.

[73] Assignee: G. D. Searle & Co., Chicago, Ill.

[21] Appl. No.: 629,718

[22] Filed: Nov. 7, 1975

[51] Int. Cl.$^2$ .................. C07D 487/04; C07D 295/14; C07D 211/52
[52] U.S. Cl. ...................... 260/268 BC; 260/326.5 D; 260/326.8; 260/293.8; 260/326.87; 260/293.54; 260/293.75; 260/583 R; 260/326.5 J; 260/326.5 R; 260/294.9; 260/296 D; 260/296 R; 260/293.67; 260/293.69; 260/326.62; 260/239 BA
[58] Field of Search .......... 260/293.8, 268 BC, 293.54, 260/293.75, 583 R, 273.71, 239 B

[56] References Cited

U.S. PATENT DOCUMENTS

| | | | |
|---|---|---|---|
| 2,881,165 | 4/1959 | Janssen et al. | 260/239 B |
| 3,318,869 | 5/1967 | Cusic et al. | 260/293.54 |
| 3,379,764 | 4/1968 | Wyness et al. | 260/583 R |
| 3,542,876 | 9/1968 | Blaney | 260/583 R |
| 3,790,581 | 2/1974 | Kreider | 260/273.71 |

*Primary Examiner*—Henry R. Jiles
*Assistant Examiner*—Cary Owens
*Attorney, Agent, or Firm*—Barbara L. Cowley; John J. Kolano

[57] ABSTRACT

Certain tertiary amines useful as pharmaceuticals are prepared in improved yields by condensing a cyclic secondary amine with a primary alkyl halide in an aqueous medium in the presence of an acid acceptor.

10 Claims, No Drawings

PROCESS FOR THE PREPARATION OF TERTIARY AMINES

BACKGROUND OF THE INVENTION

Tertiary amines have previously been prepared by the reaction of a cyclic secondary amine with a primary alkyl halide in the presence of an acid acceptor in an organic solvent. Such reactions have the multiple disadvantages of long reaction times at high temperatures and formation of various by-products.

For instance, the alkylation of 4-(4-chlorophenyl)-piperidin-4-ol with 4-chloro-1-(4-fluorophenyl)-1-butanone requires about 40 hours at the reflux temperature of about 117° C. for completion when using 4-methyl-2-pentanone as the solvent, sodium carbonate as the acid acceptor, and potassium iodide as an alkylation promoter. A modification of this procedure utilizing a 5:1 mixture of toluene and 4-methyl-2-pentanone as the reaction solvent requires 72 hours at the reflux temperature of about 110° C. for completion.

During the long heating period required by this type of procedure, the reaction mixture discolors to a considerable degree presumably due to the formation of various by-products. To remove this color from the final product requires recrystallization, and often the use of decolorizing charcoal. Such procedures are both time-consuming and expensive, and result in a lower overall yield of the desired product.

SUMMARY OF THE INVENTION

The present invention describes a new, improved synthetic process for the preparation of certain tertiary amines by condensation of a cyclic secondary amine with a primary alkyl halide in an aqueous medium in the presence of an acid acceptor. Surprisingly and unexpectedly, the use of this reaction medium provides increased yields, permits milder reaction conditions, and affords purer products. The isolation of the final product is also facilitated by the lack of large volumes of organic solvents to remove from the product and the ease of isolating the product by a simple separation.

DETAILED DESCRIPTION OF THE INVENTION

The present invention relates to a process for the preparation of tertiary amines. More particularly, this invention provides a convenient and simple route to compounds of the general formula

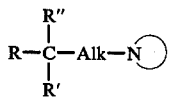
(I)

wherein Alk is a lower alkylene radical containing 2 to 6 carbon atoms; R is selected from the group consisting of lower alkyl containing 1 to 6 carbon atoms, phenyl, halophenyl, tolyl and pyridyl; R' is selected from the group consisting of lower alkyl containing 1 to 6 carbon atoms, phenyl, halophenyl, tolyl, pyridyl, cyano, and hydrogen; R" is selected from the group consisting of lower alkyl containing 1 to 6 carbon atoms, phenyl, halophenyl, tolyl, pyridyl and hydrogen; or R' and R" may together be a doubly bonded oxygen atom or both are alkoxy groups containing 1 to 6 carbon atoms or together are an ethylenedioxy or propylenedioxy group; and

is a cyclic secondary amine radical.

The lower alkyl groups referred to above contain 1 to 6 carbon atoms and are exemplified by methyl, ethyl, propyl, isopropyl and the like. The lower alkylene groups referred to above contain 2 to 6 carbon atoms and are exemplified by groups such as ethylene, propylene, trimethylene and 1,4-pentylene.

The point of attachment of the halophenyl, tolyl, or pyridyl radical is not critical. Thus, 2-tolyl, 3-tolyl, 4-tolyl, 2-pyridyl, 3-pyridyl and 4-pyridyl radicals are encompassed by the formula.

The halophenyl radicals referred to above may contain one or more bromo, chloro, fluoro or iodo atoms and include, but are not limited to, the following: 3-bromophenyl, 4-chlorophenyl, 2-fluorophenyl, 2,3,4,5,6-pentachlorophenyl, 2,5-dibromophenyl or 2-bromo-5-iodophenyl.

Illustrative of the cyclic secondary amine radicals represented by

—N⟨⟩ are the following: piperidino; (lower alkyl)piperidino [e.g., 2-, 3-, or 4-(lower alkyl)piperidino, such as 2-ethylpiperidino or 4-isopropylpiperidino]; di(lower alkyl)piperidino [e.g., 2,4-, 2,5- or 3,5-di(lower alkyl)piperidino, such as 2,4-dimethylpiperidino]; (lower alkoxy)-piperidino [e.g., 2-methoxypiperidino or 3-methoxypiperidino]; hydroxypiperidino [e.g., 3-hydroxy- or 4-hydroxypiperidino]; cyanopiperidino [e.g., 4-cyanopiperidino]; arylpiperidino [e.g., 4-phenylpiperidino or 4-tolylpiperidino]; 4-aryl-4-hydroxypiperidino [e.g., 4-hydroxy-4-phenylpiperidino or 4-(4-chlorophenyl)-4-hydroxypiperidino]; 4-aryl-4-(lower alkoxy) carbonylpiperidino [e.g., 4-ethoxycarbonyl-4-phenylpiperidino or 4-(4-chlorophenyl)-4-methoxycarbonylpiperidino]; 4-aryl-4-cyanopiperidino [e.g., 4-cyano-4-phenylpiperidino]; pyrrolidino; (lower alkyl)-pyrrolidino [e.g., 3-methylpyrrolidino]; di(lower alkyl)-pyrrolidino [e.g., 3,4-dimethylpyrrolidino]; (lower alkoxy)pyrrolidino [e.g., 2-methoxypyrrolidino]; hexamethyleneimino; azabicycloalkyl [e.g., 7-azabicyclo[2.2.1]-hept-7-yl, 2-azabicyclo[2.2.1]oct-2-yl, 2-azabicyclo[3.2.1]-oct-2-yl, 3-azabicyclo[3.2.1]oct-3-yl, 6-azabicyclo[3.2.1]-oct-6-yl, 3-azabicyclo[3.2.2]non-3-yl, 8-azabicyclo[4.3.0]-non-8-yl, 2-azabicyclo[3.2.2]non-2-yl, 2-azabicyclo[3.3.1]-non-2-yl, 3-azabicyclo[3.3.1]-non-3-yl, 2-azabicyclo[4.3.0]-non-3-yl, 7-azabicyclo[4.3.0]non-7-yl, 8-azabicyclo[4.3.1]-dec-8-yl, 2-azabicyclo[4.4.0]dec-2-yl, and 7-azabicyclo-[4.2.2]dec-7-yl]; and diazabicycloalkyl [e.g., 1,4-diazabicyclo[4.3.0]non-4-yl, and 1,4-diazabicyclo[4.4.0]dec-4-yl].

In the cyclic secondary amine radicals the lower alkyl radicals contain 1 to 6 carbon atoms. Likewise, the lower alkoxy radicals contain 1 to 6 carbon atoms in the alkyl portion. The aryl radicals are selected from the group consisting of phenyl, halophenyl, tolyl and pyridyl. The halophenyl radicals may contain one or more bromo, chloro, fluoro or iodo atoms. The point of attachment of the halophenyl, tolyl, or pyridyl radical is not critical. The azabicycloalkyl radicals contain 7 to 9 carbon atoms, and the diazabicycloalkyl radicals contain 6 to 7 carbon atoms.

The process of this invention involves the condensation of a cyclic secondary amine of the formula

wherein

is defined as hereinabove with a primary alkyl halide of the formula

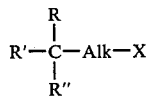

wherein X is a bromo, chloro or iodo atom; R' is selected from the group consisting of lower alkyl containing 1 to 6 carbon atoms, phenyl, halophenyl, tolyl, pyridyl, cyano, and hydrogen; R" is selected from the group consisting of lower alkyl containing 1 to 6 carbon atoms, phenyl, halophenyl, tolyl, pyridyl and hydrogen; or R' and R" are both alkoxy groups containing 1 to 6 carbon atoms or together are an ethylenedioxy or propylenedioxy group; and Alk, and R are defined as hereinabove in an aqueous medium in the presence of an acid acceptor.

Suitable acid acceptors include, but are not limited to, lithium hydroxide, potassium hydroxide, sodium hydroxide, lithium carbonate, potassium carbonate, sodium carbonate, potassium bicarbonate, and sodium bicarbonate. A particularly preferred acid acceptor for use in condensations where there are no alkali-sensitive substituents on the reactant molecules is potassium hydroxide. When the reactants contain an alkali-sensitive substituent, such as an ester, the use of a milder acid acceptor, such as potassium bicarbonate is preferred.

The reaction temperature for the present process is most preferably that of the reflux temperature of the aqueous reaction medium. Since many of the starting materials utilized in the present invention are solids at room temperature and substantially insoluble in water, the reflux temperatures cause the melting of the organic reactants and the formation of a two-phase system. In the case of low melting solid reactants or liquid reactants, lower temperatures may be utilized but this will result in a correspondingly longer reaction time.

A reaction time in the range of 2–5 hours is suitable for practicing the present invention. A particularly suitable reaction time is 3–4 hours, but this may vary depending on the nature of the reactants and the temperature at which the reaction is conducted.

In the course of the condensation reaction, certain alkali-sensitive substituents present in the starting material may react in the presence of the acid acceptor. Such is the case when R' and R" are together a double bonded oxygen atom-the molecule is thus an alkali sensitive haloketone. To minimize formation of by-products from such a compound during the alkylation, the ketone is preferably first converted to a ketal. [e.g., R' and R" are both alkoxy groups containing 1 to 6 carbon atoms or together are an ethylenedioxy or propylenedioxy group]. The ketone group is easily regenerated by the addition of an acid at the completion of the condensation reaction.

The conversion of the ketone group to the corresponding ketal is conveniently accomplished by treatment with an alcohol and an ortho ester in the presence of an acid catalyst. Methanol, ethanol, and 1,2-ethanediol are preferred alcohols while sulfuric and hydrochloric acids are the preferred acid catalysts. Methyl and ethyl orthoformate are preferred ortho esters for use in this conversion.

An alkylation promoter, such as potassium iodide, may be utilized in the present process where an alkyl chloride is one of the reactants. However, such usage is optional.

A further advantage of the present process is the ease with which the product is isolated. Since the high molecular weight products are generally rather water insoluble, they are easily extracted into a suitable organic solvent. The organic solvent can then be removed (such as by stripping under reduced pressure) to leave the pure product. Alternatively, a dilute aqueous acid solution may be added to form a salt of the desired product which is then easily separable by filtration. Depending on the nature of the final product and the type of impurities present, either of these procedures may be utilized.

The process of the present invention can be utilized to prepare numerous useful pharmaceutical compounds and intermediates useful in the synthesis of pharmaceutical compounds.

More specifically, the instant process is useful for the preparation of the compounds of British Pat. No. 1,141,664 [e.g., haloperidol, marketed as Serenace ®]; and U.S. Pat. No. 2,898,340 [e.g., diphenoxylate hydrochloride, marketed as Lomotil ®]. Additional useful compounds preparable by the instant process are those of U.S. Pat. Nos. 2,881,165 and 2,446,522; and British Patents Nos. 765,510 and 881,893.

Additionally, intermediates useful for the preparation of the compounds disclosed in U.S. Pat. Nos. 3,772,300, 3,790,581, 3,843,646, and 3,847,923, can be prepared from the present process.

The following examples describe in detail the preparation of compounds utilizing the process of the present invention. It will be apparent to those skilled in the art that many modifications, both of materials and methods, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

A mixture of 198.5 parts of 4-chloro-4'-fluorobutyrophenone, 286.0 parts of trimethyl orthoformate, 66 parts of methanol and 2.3 parts of concentrated sulfuric acid is stirred at room temperature for two hours. Then, 3.3 parts by volume of 1,1,3,3-tetramethylguanidine is added and the reaction mixture stirred for an additional 10 minutes. The solvents are removed in vacuo to leave an oily residue which is dissolved in 56 parts of methanol. To the resulting solution is added enough 50% sodium hydroxide solution to bring the pH to 11–12. Then 1.7 parts of sodium borohydride is added and the mixture stirred for 10 minutes. The off-white mixture is diluted with 140 parts of water and then extracted three times with 132 parts portion of n-hexane. The n-hexane extracts are combined and washed with a 140 parts portion of water. The aqueous extract from the previous n-hexane extractions is again extracted with a 46 parts portion of n-hexane, and all of the n-hexane extracts are combined. The combined n-hexane extracts are dried over anhydrous potassium carbonate, decolorized with carbon and filtered through celite. 0.5 Part by volume of 1,1,3,3,-tetramethylguanidine is added to the n-hexane extracts and the solvents are removed in vacuo. The resulting product, 1,1-dimethoxy-1-(4-fluorophenyl)-4-chloro-butane, exhibits nuclear magnetic resonance spectra peaks at δ=1.4(multiplet), 2.0(multiplet), 3.2(singlet), 3.4(triplet) and 7.3(multiplet), and is represented by the following structural formula.

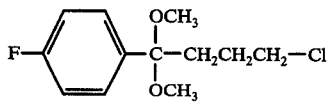

Similarly, the repetition of the above procedure using an equivalent quantity of 1-(4-tolyl)-2-methyl-3-chloro-propanone affords 1,1-dimethoxy-1-(4-tolyl)-2-methyl-3-chloro-propane.

A stirred slurry of 120.0 parts 4-(4-chlorophenyl)-piperidin-4-ol hydrochloride and 40.0 parts of potassium iodide in 500 parts of water is warmed to a temperature of about 35° C. under a nitrogen atmosphere. Then, 70.0 parts of potassium hydroxide is added. After further heating to about 55° C., 138.0 parts of 1,1-dimethoxy-1-(4-fluorophenyl)-4-chlorobutane is added. The temperature is then raised to about 102° C. and heating continued for 3.5 hours. After cooling to about 75° C., 785 parts of toluene is added to the reaction mixture and stirred for about 5 minutes. An additional 320 parts of toluene is added and the water and organic layers separated. 102 Parts of methanol is used to rinse the flask and added to the organic layer to provide a solution of 4-(4-chlorophenyl)-1-[4-(4-fluorophenyl)-4,4-dimethoxybutyl]-piperidin-4-ol. Then, 59 parts of concentrated hydrochloric acid is added to a stirred solution of the organic layer to precipitate a solid. The solid is filtered, rinsed twice with 550 parts by volume portions of a 10:9:1 acetone-toluene-methanol mixture, twice with 400 parts by volume portions of a 10:1 acetone-methanol mixture, and air-dried. The dried solid is then dissolved in 1950 parts of methanol with gentle heating on a steam bath. The resulting solution is filtered and 300 parts by volume of concentrated ammonium hydroxide is added. Heating is continued to reflux and maintained thereat for about 1 hour. Then, 2520 parts of water is added and the slurry stirred at about 75° C. for 1.5 hours. After cooling to about 25° C., the solid is filtered, washed twice with 600 parts by volume portions of a 3:1 mixture of water-methanol, and air-dried. The resulting product, 4-[4-chlorophenyl)-4-hydroxypiperidino]-4'-fluorobutyrophenone, is obtained in 32.5% yield. This product melts at about 148.5° – 150.5° C., and is represented by the following structural formula.

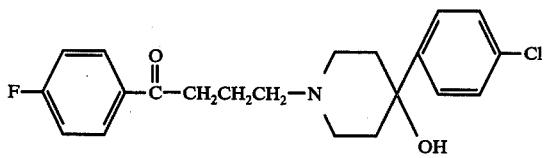

EXAMPLE 2

4.87 Parts of 4-(4-chlorophenyl)piperidin-4-ol, 1.91 parts of potassium iodide and 25 parts of deionized water is stirred together and gently warmed under a nitrogen atmosphere. Then, 2.75 parts of potassium bicarbonate and 6.17 parts of 1,1-dimethoxy-1-(4-fluorophenyl)-4-chlorobutane is added and the mixture is heated to reflux. After heating for 4.5 hours, the reaction mixture is allowed to cool to room temperature and 55 parts of toluene is added. The aqueous and organic layers are separated, and the aqueous layer discarded. 5.1 Parts of methanol is added to the organic layer. Then, 2.5 parts of concentrated hydrochloric acid is added with vigorous stirring. The resulting precipitate is cooled to about 25° C., filtered, washed twice with 22 parts by volume portions of a 10:9:1 mixture of acetone-toluene-methanol, and twice with 20 parts by volume portions of a 10:1 mixture of acetone-methanol. After air-drying, the product, 4-[4-(4-chlorophenyl)-4-hydroxypiperidino]-4'-fluorobutyrophenone hydrochloride, melts at about 227°–229° C. and is obtained in 80.1% yield. This compound is the hydrochloride salt of the product of Example 1.

EXAMPLE 3

Under a nitrogen atmosphere 4.87 parts of 4-(4-chlorophenyl)piperidin-4-ol, 1.91 parts of potassium iodide and 25 parts of deionized water is combined and gently warmed. 1.65 Parts of potassium hydroxide, followed by 6.12 parts of 1,1-ethylenedioxy-1-(4-fluorophenyl)-4-chlorobutane is added, and the mixture is heated to reflux. After refluxing for 3.75 hours, the reaction mixture is cooled to room temperature, and 55 parts of toluene is added. The aqueous and organic layers are separated, and the aqueous layer discarded. 5.1 Parts of methanol is added to the organic layer and the mixture cooled to about 25° C. While stirring vigorously, 3.1 parts of concentrated hydrochloric acid is added. The resultant precipitate is filtered and washed twice with 22 parts by volume portions of a 10:9:1 mixture of acetone-toluene-methanol. The filtrate, after standing for about 18 hours, affords additional precipitate. This is filtered and combined with the initially isolated precipitate. The solid is then washed twice with 22 parts by volume portions of a 10:9:1 mixture of acetone-toluene-methanol and twice with 22 parts by volume portions of a 10:1 mixture of acetone-methanol. The solid is air-dried to give, in 75.5% yield, 4-[4-(4-chlorophenyl)-4-hydroxypiperidino]-4'-fluorobutyrophenone hydrochloride as a white solid melting at about 226° – 228° C., and identical to the product of Example 2.

EXAMPLE 4

When an equivalent quantity of piperidine is substituted for the 4-(4-chlorophenyl)piperidin-4-ol used in Example 3, and the procedure detailed therein substantially repeated, there is obtained 4-piperidino-4'-fluorobutyrophenone hydrochloride, melting at about 180° – 181° C.

EXAMPLE 5

The use of an equivalent quantity of 4-(4-tolyl)-piperidin-4-ol in place of the 4-(4-chlorophenyl)-piperidin-4-ol used in Example 3, and the substantial repetition of the procedure detailed therein affords 4-[4-(4-tolyl)-4-hydroxypiperidino]-4'-fluorobutyrophenone hydrochloride, melting at about 216° – 218° C.

EXAMPLE 6

Substitution of equivalent quantities of 1,1-dimethoxy-1-(4-tolyl)-2-methyl-3-chloropropane and piperidine for the 1,1-dimethoxy-1-(4-fluorophenyl)-4-chlorobutane and the 4-(4-chlorophenyl)piperidin-4-ol used in Example 3, and substantial repetition of the procedure detailed therein, affords 1-(4-tolyl)-2-methyl-3-piperidinopropanone hydrochloride, melting at about 176° – 177° C.

EXAMPLE 7

To a stirred mixture of 78.5 parts of 2,2-diphenyl-4-bromobutyronitrile, 19.7 parts of potassium iodide and 30.0 parts of 1,4-diazabicyclo[4.3.0]nonane is added 70 parts of water and 19.3 parts of potassium hydroxide under a nitrogen atmosphere. The mixture is stirred and heated to 75° – 80° C. and then further heated to reflux (108° – 112° C.). After 3.5 hours of heating at reflux, the mixture is cooled to about 25° C. and 180 parts of ethyl ether added. The resulting organic layer is extracted once with a 20% solution of hydrochloric acid in water followed by a further extraction with 6% solution of hydrochloric acid in water. The aqueous extracts are then combined and basified to pH 11.0 with a 50% solution of sodium hydroxide in water. The resulting oil is extracted with three 110 parts portions of ethyl ether. The ether extracts are combined, dried over anhydrous potassium carbonate, and stripped of solvent under reduced pressure. The resulting product, 2,2-diphenyl-4-(1,4-diazabicyclo[4.3.0]non-4-yl)butyronitrile, is obtained in 89% yield. Correction of this yield to reflect the purity of the 1,4-diazabicyclo[4.3.0]nonane (96%) results in a yield of 93% for this reaction. This product boils at about 190° – 210° C. at 0.1 mm. pressure and is represented by the following structural formula.

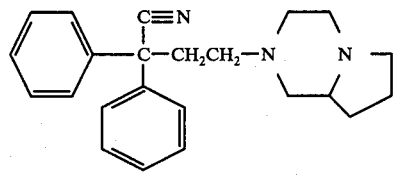

EXAMPLE 8

To 70.6 parts of 2,2-diphenyl-4-bromobutyronitrile is added 27 parts of 1,4-diazabicyclo[4.3.0]nonane, 63 parts of demineralized water and 15.5 parts of potassium hydroxide. The mixture is stirred and heated to 75° – 80° C. and then further heated to reflux. After 3.5 hours at reflux, the mixture is cooled to about 30° C. and 180 parts of ethyl ether is added. The aqueous layer is separated and discarded. The remaining ether layer is extracted three times with 100 parts by volume portions of 1% acetic acid in water, twice with 30% solutions of hydrochloric acid in water, and twice with 50% solutions of hydrochloric acid in water. The hydrochloric acid solution extracts are combined and basified to pH 11.0 with a 50% solution of potassium hydroxide in water. The resulting oil is extracted with three 150 part portions of chloroform. The chloroform extracts are combined, washed with 100 parts of a saturated sodium chloride solution, dried over anhydrous potassium carbonate, and stripped of solvent under reduced pressure. The resulting product, 2,2-diphenyl-4-(1,4-diazabicyclo[4.3.0]non-4-yl)butyronitrile, identical to the product of Example 7, is obtained in 86% yield. Correction of this yield to reflect the purity of the 1,4-diazabicyclo[4.3.0]-nonane (86.4%) results in a yield of 99.5% for this reaction.

EXAMPLE 9

The use of equivalent quantities of 1,1-diphenyl-3-chloropropane and hexamethyleneimine in place of the 2,2-diphenyl-4-bromobutyronitrile and the 1,4-diazabicyclo[4.3.0]-nonane used in Example 7, and the substantial repetition of the procedure detailed therein, affords 1-(3,3-diphenylpropyl)hexamethyleneimine, boiling at about 170° – 174° C. at 1 mm. pressure.

EXAMPLE 10

Substitution of equivalent quantities of 2-phenyl-2-(3-pyridyl)-4-bromobutyronitrile and 2-azabicyclo[2.2.2.]octane for the 2,2-diphenyl-4-bromobutyronitrile and the 1,4-diazabicyclo[4.3.0]nonane used in Example 7, and the substantial repetition of the procedure detailed therein affords 2-phenyl-2-(3-pyridyl)-4-(2-azabicyclo[2.2.2.]oct-2-yl)butyronitrile.

EXAMPLE 11

When equivalent quantities of 2-phenyl-2-(4-pyridyl)-4-bromobutyronitrile and 3-azabicyclo[3.2.2.]nonane are used in place of the 2,2-diphenyl-4-bromobutyronitrile and the 1,4-diazabicyclo[4.3.0]nonane used in Example 7, and the procedure detailed therein substantially repeated, there is obtained 2-phenyl-2-(4-pyridyl)-4-(3-azabicyclo[3.2.2]non-3-yl)butyronitrile. This compound is represented by the following structural formula.

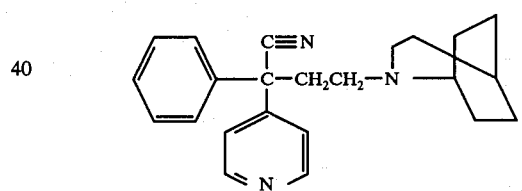

EXAMPLE 12

To a stirred solution of 0.85 part of 2-azabicyclo-[2.2.2.]octane hydrochloride in 20 parts of water is added 0.71 part of potassium hydroxide under a nitrogen atmosphere. Then, 1.90 parts of 2,2-diphenyl-4-bromobutyronitrile is added, and the mixture heated to reflux for 3.5 hours. This reaction mixture is cooled to about 60° C., whereupon 13 parts of benzene is added. The aqueous layer is separated and extracted with 15 parts of benzene. To the combined benzene extracts is added dropwise 2 parts by volume of a solution of hydrochloric acid in isopropanol. The volume of this solution is reduced by heating on a steam bath. Cooling affords a white precipitate which is washed with benzene and dried at 100° C. for about 2 hours. The resulting product, 2,2-diphenyl-4-(2-azabicyclo[2.2.2]oct-2-yl)butyronitrile hydrochloride, is obtained in approximately 76.8% yield. This product melts at about 194° – 197° C., and is represented by the following structural formula.

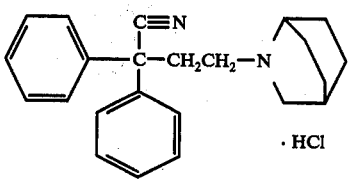

·HCl

EXAMPLE 13

To a stirred solution of 13.7 parts of potassium hydroxide in 275 parts water is added 33.0 parts of 2,2-diphenyl-4-bromobutyronitrile. Then, 14.8 parts of 2-azabicyclo[2.2.2.]octane hydrochloride is added and the mixture heated to reflux temperature. After refluxing for 5 hours, the mixture is cooled to room temperature. The resulting solid is filtered and washed with 100 parts of water. After air-drying, the solid is dissolved in 175 parts of benzene and 200 parts by volume of a 10% solution of hydrochloric acid in water is added. The oil which separates is allowed to solidify and the solid is separated by filtration. The filtrate is washed twice with 200 part portions of methylene chloride and the methylene chloride washings are then used to dissolve the previously filtered solid. To the resulting solution is added 150 parts by volume of a 1M potassium carbonate solution. After stirring for two hours, the methylene chloride extracts are combined and dried over sodium sulfate. The methylene chloride solvent is then evaporated under reduced pressure to leave a white solid. This solid is recrystallized from a mixture of n-hexane and acetone to give 2,2-diphenyl-4-(2-azabicyclo[2.2.2.]oct-2-yl)butyronitrile, melting at about 93° – 95° C., in a 83.5% yield. This compound is the free base of the product of Example 12.

EXAMPLE 14

Substitution of an equivalent quantity of 4-methylpiperidine hydrochloride for the 2-azabicyclo[2.2.2]octane hydrochloride used in Example 12, and substantial repetition of the procedure described therein, affords 2,2-diphenyl-4-(4-methylpiperidino)butyronitrile hydrochloride, melting at 189° – 191° C.

EXAMPLE 15

When an equivalent quantity of pyrrolidine hydrochloride is substituted for the 2-azabicyclo[2.2.2]octane hydrochloride used in Example 12, and the procedure described therein substantially repeated, there is obtained 2,2-diphenyl-4-pyrrolidinobutyronitrile hydrochloride, melting at 207° – 208° C.

EXAMPLE 16

Substitution of an equivalent quantity of 2,5-dimethylpyrrolidine hydrochloride for the 2-azabicyclo[2.2.2]-octane hydrochloride used in Example 12, and substantial repetition of the procedure described therein affords 2,2-diphenyl-4-(2,5-dimethylpyrrolidino)butyronitrile hydrochloride, melting at 177° – 179° C.

EXAMPLE 17

The use of an equivalent quantity of 1,1,1-triphenyl-3-chloropropane for the 2,2-diphenyl-4-bromobutyronitrile of Example 12, and the substantial repetition of the procedure detailed therein, affords 2-(3,3,3-triphenylpropyl)-2-azabicyclo[2.2.2]octane hydrochloride, melting at about 222° – 223° C., and represented by the following structural formula.

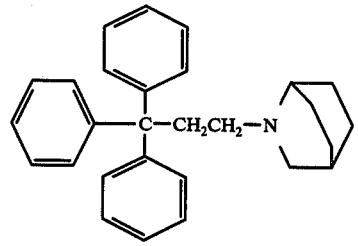

EXAMPLE 18

When equivalent quantities of piperidine hydrochloride and 2-phenyl-2-(2-chloroethyl)butyronitrile are substituted for the 2-azabicyclo[2.2.2]octane hydrochloride and 2,2-diphenyl-4-bromobutyronitrile used in Example 12, and the procedure described therein substantially repeated, there is obtained 2-phenyl-2-ethyl-4-piperidino-butyronitrile hydrochloride melting at about 200° – 203° C.

EXAMPLE 19

Repetition of the procedure detailed in Example 12 using piperidine hydrochloride and 1,1-diphenyl-3-chloropropane in place of the 2-azabicyclo[2.2.2]octane hydrochloride and 2,2-diphenyl-4-bromobutyronitrile affords 1-(3,3-diphenylpropyl)piperidine hydrocloride, melting at about 216° – 217° C., and represented by the following structural formula.

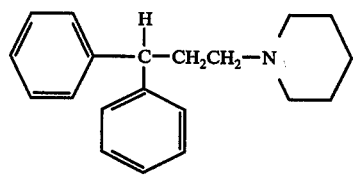

EXAMPLE 20

To 27.7 parts of 4-phenyl-4-ethoxycarbonylpiperidine is added 9.88 parts of potassium iodide and 130 parts of deionized water under a nitrogen atmosphere. The mixture is gently warmed and 14.22 parts of potassium bicarbonate is slowly added. When the temperature reaches about 60° – 70° C., 38.7 parts of 2,2-diphenyl-4-bromobutyronitrile is added and the heating continued until reflux. After refluxing for 4.0 hours, the reaction mixture is cooled, and 119 parts of tetrahydrofuran and 72 parts of n-heptane are added. The organic layer is separated, washed twice with 250 parts by volume portions of a saturated sodium chloride solution, and filtered. Then, 119 parts of tetrahydrofuran and 420 parts of n-heptane are added. A solution of 62 parts of concentrated hydrochloric acid in 155 parts of water is added dropwise to the organic layer with vigorous stirring. The resultant white precipitate is filtered and dried, after cooling to about 10° C., to afford, in 90.5% yield, 1-(3-cyano-3,3-diphenylpropyl)-4-phenylisonipecotic acid ethyl ester hydrochloride.

Recrystallization from 150 parts of methylene chloride and 835 parts isopropanol affords white crystals melting at 224° – 226.5° C. in a yield from the starting amine of 79.5%. This product is represented by the following structural formula.

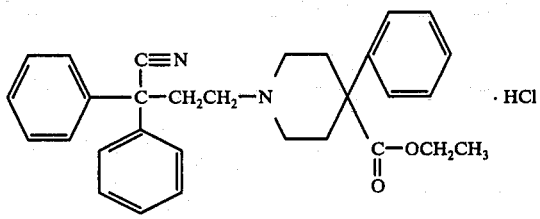

EXAMPLE 21

A solution of 4.87 parts of 4-(4-chlorophenyl)piperidin-4-ol and 1.91 parts of potassium iodide in 25 parts of deionized water is heated and stirred under a nitrogen atmosphere. When the temperature reaches about 30° - 35° C., 1.65 parts of potassium hydroxide is added. The heating is continued to a temperature of about 45° - 55° C., at which time 7.51 parts of 2,2-diphenyl-4-bromobutyronitrile is added. The temperature is raised to reflux and maintained thereat for 4.5 hours. After cooling to about 30° C., 29 parts of ethyl ether is added with stirring. The ether and water layers are separated and the water layer re-extracted with 7 parts of ethyl ether. The ether extracts are combined and washed twice with 12 part portions of dilute acetic acid. A solution of hydrochloric acid in isopropanol is added to form a precipitate which is filtered, washed with ethyl ether, and air-dried. The dried soild, 2,2-diphenyl-4-[4-(4-chlorophenyl)-4-hydroxypiperidino]butyronitrile hydrochloride is obtained in 90.7% yield. The solid is dissolved in dilute ammonium hydroxide and extracted with ethyl ether. The solvent is removed from the ether extract under reduced pressure to afford as a white glass, 2,2-diphenyl-4-[4-(4-chlorophenyl)-4-hydroxypiperidino]-butyronitrile, represented by the following structural formula.

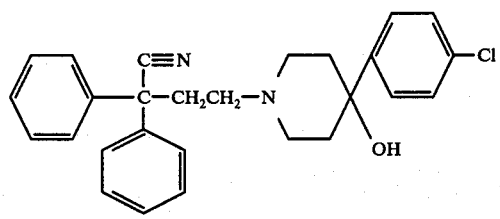

EXAMPLE 22

To 1.96 parts of piperidine is added 1.91 parts of potassium iodide and 25 parts of deionized water under a nitrogen atmosphere. The mixture is gently warmed and 1.65 parts of potassium hydroxide and 7.51 parts of 2,2-diphenyl-4-bromobutyronitrile are added. The temperature is raised to reflux and maintained thereat for 4.5 hours. After cooling to room temperature, the reaction mixture is extracted three times with 14 part portions of ethyl ether. The ether extracts are combined, and extracted four times with 25 parts by volume portions of a dilute acetic acid solution. The acid extracts are combined, neutralized to about pH 10 with 50% sodium hydroxide solution, and extracted again with ethyl ether. The ether extracts are combined, washed twice with 50 parts by volume portions of a saturated sodium chloride solution, and dried over anhydrous potassium carbonate. The solvent is removed under reduced pressure to afford, as an off-white solid, in 86.1% yield, 2,2-diphenyl-4-piperidinobutyronitrile. This compound melts at 74° - 77° C., and is represented by the following structural formula.

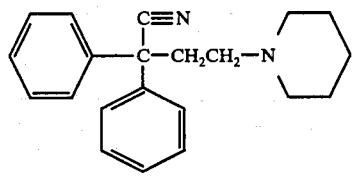

EXAMPLE 23

1.96 Parts piperidine, 1.91 parts potassium iodide and 25 parts deionized water are combined and gently heated under a nitrogen atmosphere. To this slurry is then added 2.75 parts of potassium bicarbonate, followed by 7.51 parts of 2,2-diphenyl-4-bromobutyronitrile. The mixture is heated to reflux and maintained thereat for 4.5 hours. After cooling to room temperature, the reaction mixture is extracted three times with 14 part portions of ethyl ether. The ether extracts are combined, and extracted six times with 25 parts by volume portions of dilute acetic acid solution. The acid extracts are combined, basified to about pH 10 - 12 with 50% sodium hydroxide solution, and again extracted with ethyl ether. The ether extracts are combined, washed with water and saturated sodium chloride solution, and dried over anhydrous potassium carbonate. Removal of the solvent affords 2,2-diphenyl-4-piperidinobutyronitrile, identical to the product of Example 22, in a 66.6% yield.

EXAMPLE 24

To a warmed mixture of 1.96 parts piperidine, 1.91 parts potassium iodide and 25 parts deionized water under a nitrogen atmosphere is added 3.46 parts potassium bicarbonate and 7.51 parts of 2,2-diphenyl-4-bromobutyronitrile. The mixture is heated to reflux and maintained thereat for 4.5 hours. After cooling to room temperature, the reaction mixture is extracted three times with 14 part portions of ethyl ether. The ether extracts are combined, and extracted six times with 25 parts by volume portions of dilute acetic acid solution. The acid extracts are combined, basified to about pH 10 - 12 with 50% sodium hydroxide solution, and again extracted with ethyl ether. The ether extracts are combined and dried over anhydrous potassium carbonate. Removal of the solvent affords 2,2-diphenyl-4-piperidinobutyronitrile, identical to the product of Example 22, in a 75.3% yield.

EXAMPLE 25

Substitution of an equivalent quantity of 2,2-diphenyl-5-chlorovaleronitrile for the 2,2-diphenyl-4-bromobutyronitrile, and 1,4-diazabicyclo[4.4.0]decane for the piperidine used in Example 22, and substantial repetition of the procedure detailed therein, affords 2,2-diphenyl-5-(1,4-diazabicyclo[4.4.0]dec-4-yl)valeronitrile dihydrochloride, melting at about 233° - 238° C. with decomposition.

EXAMPLE 26

Using an equivalent quantity of 2,2-diphenyl-5-chlorovaleronitrile in place of the 2,2-diphenyl-4-bromobutyronitrile, and 3-azabicyclo[3.2.2]nonane in place of the piperidine used in Example 22, and substantially repeating the procedure detailed therein, affords 2,2-diphenyl-5-(3-azabicyclo[3.2.2]non-3-yl)valeronitrile hydrochloride, melting at about 272° - 273° C. This compound is represented by the following structural formula.

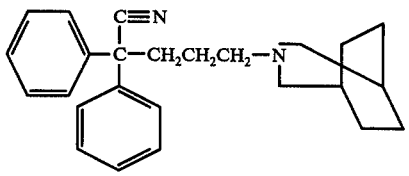

EXAMPLE 27

To a heated slurry of 2.90 parts of 1,4-diazabicyclo[4.3.0]nonane, 1.91 parts of potassium iodide, and 25 parts of deionized water is added 1.65 parts potassium hydroxide and 6.17 parts of 1,1-dimethoxy-1-(4-fluorophenyl)-4-chlorobutane under nitrogen. The mixture is heated to reflux and held at that temperature for 4.5 hours. After cooling to room temperature, 18 parts of ethyl ether and a sufficient quantity of concentrated hydrochloric acid to bring the pH of the aqueous phase to about 2 are added. The aqueous layer is separated and basified to pH 12 with 50% sodium hydroxide solution. The resultant oil which forms is extracted into chloroform. The solvent is removed under reduced pressure to afford an orange oil. Chromatography of this oil using silica gel as an adsorbant and mixtures of ethanol (0.5 – 20%) in methylene chloride with 0.25% ammonium hydroxide as eluants affords 4-(1,4-diazabicyclo[4.3.0]-non-4-yl)-4'-fluorobutyrophenone as an orange oil, in yield of 49%. This compound is represented by the following structural formula.

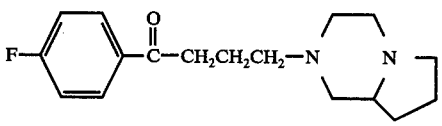

What is claimed is:
1. A process for the preparation of tertiary amines of the general formual

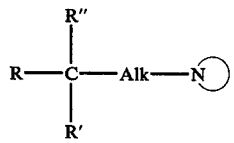

wherein Alk is a lower alkylene radical containing 2 to 6 carbon atoms; R is selected from the group consisting of lower alkyl containing 1 to 6 carbon atoms, phenyl, halophenyl, tolyl and pyridyl; R' is selected from the group consisting of lower alkyl containing 1 to 6 carbon atoms, phenyl, halophenyl, tolyl, pyridyl, cyano, and hydrogen; R" is selected from the group consisting of lower alkyl containing 1 to 6 carbon atoms, phenyl, halophenyl, tolyl, pyridyl and hydrogen; or R' and R" may together be a doubly bonded oxygen atom or both are alkoxy groups containing 1 to 6 carbon atoms or together are an ethylenedioxy or propylenedioxy group; and

is a cyclic secondary amine radical; which comprises contacting a cyclic secondary amine of the formula

wherein

is defined as hereinabove with a primary alkyl halide of the formula

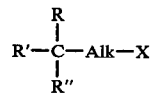

wherein X is a bromo, chloro or iodo atom; R' is selected from the group consisting of lower alkyl containing 1 to 6 carbon atoms, phenyl, halophenyl, tolyl, pyridyl, cyano, hydrogen; R" is selected from the group consisting of lower alkyl containing 1 to 6 carbon atoms, phenyl, halophenyl, tolyl, pyridyl and hydrogen; or R' and R" are both alkoxy groups containing 1 to 6 carbon atoms or together are a ethylenedioxy or propylenedioxy group; and Alk, and R are defined as hereinabove in a two phase aqueous medium in the presence of an inorganic base acid acceptor, optionally followed by hydrolysis of a ketal to afford the corresponding ketone.

2. The process according to claim 1 wherein the acid acceptor is potassium hydroxide.

3. The process according to claim 1 wherein the acid acceptor is potassium bicarbonate.

4. The process according to claim 1 for the preparation of 4-[4-(4-chlorophenyl)-4-hydroxypiperidino]-4'-fluorobutyrophenone which comprises contacting a 4-(4-chlorophenyl)piperidin-4-ol with a primary alkyl halide of the formula

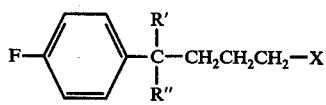

wherein X is a bromo, chloro or iodo atom and R' and R" are both alkoxy groups containing 1 to 6 carbon atoms or together are an ethylenedioxy or propylenedioxy group.

5. The process according to claim 1 for the preparation of 4-[4-(4-chlorophenyl)-4-hydroxypiperidino]-4'-fluorobutyrophenone which comprises contacting 4-(4-chloro-phenyl)piperidin-4-ol with 1,1-dimethoxy-1-(4-fluorophenyl)-4-chlorobutane and hydrolyzing the resulting ketal compound to the ketone product.

6. The process according to claim 1 for the preparation of 2,2-diphenyl-4-(1,4-diazabicyclo[4.3.0]non-4-yl)butyronitrile which comprises contacting 1,4-diazabicyclo-[4.3.0]nonane with 2,2-diphenyl-4-bromobutyronitrile.

7. The process according to claim 1 for the preparation of 2,2-diphenyl-4-(2-azabicyclo[2.2.2]oct-2-yl)butyronitrile which comprises contacting 2-azabicyclo[2.2.2]octane with 2,2-diphenyl-4-bromobutyronitrile.

8. The process according to claim 1 for the preparation of 1-(3-cyano-3,3-diphenylpropyl)-4-phenylisonipecotic acid ethyl ester which comprises contacting 4-phenyl-4-ethoxycarbonylpiperidine with 2,2-diphenyl-4-bromobutyronitrile.

9. The process according to claim 1 for the preparation of 2,2-diphenyl-4-[4-(4-chlorophenyl)-4-hydroxypiperidino]butyronitrile which comprises contacting 4-(4-chlorophenyl)piperidin-4-ol with 2,2-diphenyl-4-bromobutyronitrile.

10. The process according to claim 1 for the preparation of 2,2-diphenyl-4-piperidinobutyronitrile which comprises contacting piperidine with 2,2-diphenyl-4-bromobutyronitrile.

* * * * *